(12) United States Patent
Manchester

(10) Patent No.: US 11,924,374 B2
(45) Date of Patent: Mar. 5, 2024

(54) SYSTEM FOR REAL TIME, REMOTE ACCESS TO AND ADJUSTMENT OF PATIENT HEARING AID WITH PATIENT IN NORMAL LIFE ENVIRONMENT

(71) Applicant: Cochlear Limited, Macquarie University, Macquarie University (AU)

(72) Inventor: Deborah M. Manchester, Studio City, CA (US)

(73) Assignee: Cochlear Limited, Macquarie University (AU)

( * ) Notice: Subject to any disclaimer, the term of this patent is extended or adjusted under 35 U.S.C. 154(b) by 0 days.

(21) Appl. No.: 17/834,883

(22) Filed: Jun. 7, 2022

(65) Prior Publication Data

US 2022/0311863 A1 Sep. 29, 2022

Related U.S. Application Data

(63) Continuation of application No. 16/846,184, filed on Apr. 10, 2020, now Pat. No. 11,375,061, which is a
(Continued)

(51) Int. Cl.
*H04M 3/42* (2006.01)
*G16H 40/67* (2018.01)
*H04R 25/00* (2006.01)

(52) U.S. Cl.
CPC ........ *H04M 3/42391* (2013.01); *G16H 40/67* (2018.01); *H04M 3/42136* (2013.01);
(Continued)

(58) Field of Classification Search
CPC ......... H04M 3/42391; H04M 3/42136; H04M 2203/053; G16H 40/67; G16H 20/30;
(Continued)

(56) References Cited

U.S. PATENT DOCUMENTS

| 4,441,210 A | 4/1984 | Hochmair et al. |
| 4,577,641 A | 3/1986 | Hochmair et al. |

(Continued)

FOREIGN PATENT DOCUMENTS

| AU | 2012369343 A1 * | 8/2014 | ............ H04R 25/70 |
| CN | 104270705 A | 1/2015 | |

(Continued)

OTHER PUBLICATIONS

"[Redacted Version of Document Proposed to be Filed Under Seal] Declaration of Dr. Heike Heuermann in Support of Defendants Sivantos GMBH's and Sivantos,Inc.'s Opposition to Plaintiffs Motion for Preliminary Injunction," Jul. 30, 2018, 16 pages, Case No. 2:17-cv-05309-ODW (JEMx), US Dist. Ct. Central District of California.

(Continued)

*Primary Examiner* — Angelica M McKinney
(74) *Attorney, Agent, or Firm* — Piloff Passino & Cosenza LLP; Martin J. Cosenza

(57) ABSTRACT

Real time, remote access to and adjustment of the hearing aid of a patient while the patient is located in a normal life environment that is remote from a hearing professional. A session request initiates a programming session. Adjustable settings from the patient's hearing aid are wirelessly streamed to the patient's mobile device and from the mobile device to a streaming cloud server. The settings are stored on the cloud, streamed from the cloud to a hearing professional's computer or mobile device and displayed. The hearing professional then changes at least one of the adjustable hearing aid settings and the changed settings are streamed to the cloud, stored on the cloud, streamed from the cloud to the patient's mobile device, wirelessly transmitted to the hearing aid and stored there. A telephonic voice connection between the hearing professional and the patient's mobile
(Continued)

device is used to transmit the patient's evaluation of changed settings to the hearing professional.

17 Claims, 3 Drawing Sheets

Related U.S. Application Data continuation of application No. 16/428,337, filed on May 31, 2019, now Pat. No. 10,623,564, which is a continuation of application No. 15/158,667, filed on May 19, 2016, now Pat. No. 10,348,891.

(60) Provisional application No. 62/215,032, filed on Sep. 6, 2015.

(52) U.S. Cl.
CPC ............ H04R 25/554 (2013.01); H04R 25/70 (2013.01); *H04M 2203/053* (2013.01); *H04R 2225/55* (2013.01)

(58) Field of Classification Search
CPC .. H04R 25/554; H04R 25/70; H04R 2225/55; H04R 25/55; H04R 25/50
See application file for complete search history.

(56) References Cited

U.S. PATENT DOCUMENTS

| | | |
|---|---|---|
| 5,024,224 A | 6/1991 | Engebretson |
| 5,069,210 A | 12/1991 | Jeutter et al. |
| 5,085,628 A | 2/1992 | Engebretson et al. |
| 5,531,774 A | 7/1996 | Schulman et al. |
| 5,569,307 A | 10/1996 | Schulman et al. |
| 5,571,148 A | 11/1996 | Loeb et al. |
| 5,603,726 A | 2/1997 | Schulman et al. |
| 5,609,616 A | 3/1997 | Schulman et al. |
| 5,702,342 A | 12/1997 | Metzler et al. |
| 5,707,338 A | 1/1998 | Adams et al. |
| 5,749,909 A | 5/1998 | Schroeppel et al. |
| 5,772,575 A | 6/1998 | Lesinski et al. |
| 5,776,172 A | 7/1998 | Schulman et al. |
| 5,788,711 A | 8/1998 | Lehner et al. |
| 5,795,287 A | 8/1998 | Ball et al. |
| 5,842,967 A | 12/1998 | Kroll |
| 5,857,958 A | 1/1999 | Ball et al. |
| 5,876,425 A | 3/1999 | Gord et al. |
| 5,879,283 A | 3/1999 | Adams et al. |
| 5,899,847 A | 5/1999 | Adams et al. |
| 5,938,691 A | 8/1999 | Schulman et al. |
| 5,954,628 A | 9/1999 | Kennedy |
| 5,991,663 A | 11/1999 | Irlicht et al. |
| 5,993,376 A | 11/1999 | Kennedy |
| 5,997,446 A | 12/1999 | Stearns |
| 5,997,466 A | 12/1999 | Adams et al. |
| 5,999,856 A | 12/1999 | Kennedy |
| 6,001,129 A | 12/1999 | Bushek et al. |
| 6,005,955 A | 12/1999 | Kroll et al. |
| 6,067,474 A | 5/2000 | Schulman et al. |
| 6,077,215 A | 6/2000 | Leysieffer |
| 6,154,023 A | 11/2000 | Durand |
| 6,190,306 B1 | 2/2001 | Kennedy |
| 6,342,035 B1 | 1/2002 | Kroll et al. |
| 6,390,970 B1 | 5/2002 | Müller |
| 6,398,717 B1 | 6/2002 | Leysieffer et al. |
| 6,540,661 B1 | 4/2003 | Müller |
| 6,554,762 B2 | 4/2003 | Leysieffer |
| 6,603,860 B1 | 8/2003 | Taenzer et al. |
| 6,620,094 B2 | 9/2003 | Miller |
| 6,651,501 B1 | 11/2003 | Willis |
| 6,712,754 B2 | 3/2004 | Miller et al. |
| 6,785,394 B1 | 8/2004 | Olsen et al. |
| 6,788,790 B1 | 9/2004 | Leysieffer |
| 6,850,775 B1 | 2/2005 | Berg |
| 6,879,692 B2 | 4/2005 | Nielsen et al. |
| 6,879,693 B2 | 4/2005 | Miller et al. |
| 6,978,155 B2 | 12/2005 | Berg |
| 6,997,864 B2 | 2/2006 | Conn et al. |
| 7,137,946 B2 | 11/2006 | Waldmann |
| 7,149,773 B2 | 12/2006 | Haller et al. |
| 7,283,842 B2 | 10/2007 | Berg |
| 7,302,069 B2 | 11/2007 | Niederdränk et al. |
| 7,447,319 B2 | 11/2008 | Miller et al. |
| 8,005,232 B2 | 8/2011 | Roeck et al. |
| 8,194,902 B2 | 6/2012 | Pedersen |
| 8,238,592 B2 | 8/2012 | Norgaard et al. |
| 8,280,086 B2 | 10/2012 | Topholm |
| 8,452,036 B2 | 5/2013 | Sommer et al. |
| 8,503,703 B2 | 8/2013 | Eaton et al. |
| 8,542,842 B2 | 9/2013 | Zaccaria |
| 8,654,986 B2 | 2/2014 | Caballero Catoira |
| 8,657,759 B2 | 2/2014 | Tsay et al. |
| 8,777,869 B2 | 7/2014 | Givens et al. |
| 8,849,202 B2 | 9/2014 | Linde et al. |
| 8,891,793 B1 | 11/2014 | Sacha et al. |
| 8,965,016 B1 | 2/2015 | Howes |
| 8,965,017 B2 | 2/2015 | Bryant et al. |
| 8,971,556 B2 | 3/2015 | Fleizach et al. |
| 9,107,016 B2 | 8/2015 | Shennib |
| 9,173,043 B2 | 10/2015 | Bulow et al. |
| 9,204,226 B2 | 12/2015 | Sigwanz et al. |
| 9,227,057 B2 | 1/2016 | McElveen, Jr. |
| 9,247,361 B2 | 1/2016 | Nishizaki et al. |
| 9,323,893 B2 | 4/2016 | Berry et al. |
| 9,344,817 B2 | 5/2016 | Eaton et al. |
| 9,357,317 B2 | 5/2016 | Eaton et al. |
| 9,374,647 B2 * | 6/2016 | Han .................... H04R 25/50 |
| 9,509,950 B2 * | 11/2016 | Kobayashi ............ H04W 4/50 |
| 9,516,438 B2 | 12/2016 | Andersen et al. |
| 9,516,439 B2 | 12/2016 | Westergaard et al. |
| 9,565,500 B2 | 2/2017 | Kim et al. |
| 9,613,028 B2 | 4/2017 | Foo et al. |
| 9,639,342 B2 | 5/2017 | Kryzer |
| 9,723,415 B2 | 8/2017 | Gran et al. |
| 9,774,965 B2 | 9/2017 | Siddhartha et al. |
| 9,883,297 B2 | 1/2018 | Ungstrup et al. |
| 10,129,664 B2 | 11/2018 | Fitz et al. |
| 10,154,356 B2 | 12/2018 | Bazzoni |
| 10,348,891 B2 * | 7/2019 | Manchester ...... H04M 3/42391 |
| 10,510,446 B2 | 12/2019 | Westermann et al. |
| 10,602,285 B2 | 3/2020 | Bryant et al. |
| 10,623,564 B2 * | 4/2020 | Manchester ........... H04R 25/70 |
| 10,652,676 B2 | 5/2020 | Westermann et al. |
| 10,667,062 B2 | 5/2020 | Westergaard et al. |
| 10,783,996 B2 | 9/2020 | Westermann et al. |
| 10,904,677 B2 | 1/2021 | Westermann et al. |
| 10,932,071 B2 | 2/2021 | Solum et al. |
| 11,240,608 B2 | 2/2022 | Bisgaard et al. |
| 11,375,061 B2 * | 6/2022 | Manchester ......... H04R 25/554 |
| 2003/0097037 A1 | 5/2003 | Miller |
| 2003/0204131 A1 | 10/2003 | Aschoff et al. |
| 2004/0081328 A1 | 4/2004 | Leedom et al. |
| 2005/0010260 A1 | 1/2005 | Gerber |
| 2005/0036637 A1 | 2/2005 | Janssen |
| 2005/0107831 A1 | 5/2005 | Hill et al. |
| 2005/0143781 A1 | 6/2005 | Carbunaru et al. |
| 2006/0062412 A1 | 3/2006 | Berg |
| 2006/0184212 A1 | 8/2006 | Faltys et al. |
| 2006/0190059 A1 | 8/2006 | Griffith |
| 2007/0009123 A1 | 1/2007 | Aschoff et al. |
| 2007/0050212 A1 | 3/2007 | Kearby et al. |
| 2007/0098195 A1 | 5/2007 | Holmes |
| 2007/0156204 A1 | 7/2007 | Denker et al. |
| 2007/0179565 A1 | 8/2007 | Overstreet et al. |
| 2008/0037798 A1 | 2/2008 | Baechler et al. |
| 2008/0056518 A1 | 3/2008 | Burrows et al. |
| 2008/0085023 A1 | 4/2008 | Kulkarni et al. |
| 2008/0123865 A1 | 5/2008 | Beck |
| 2009/0118796 A1 | 5/2009 | Chen et al. |
| 2009/0154741 A1 | 6/2009 | Woods et al. |
| 2010/0142737 A1 | 6/2010 | Roeck et al. |
| 2010/0145411 A1 | 6/2010 | Spitzer |

(56) References Cited

U.S. PATENT DOCUMENTS

| | | | |
|---|---|---|---|
| 2010/0222847 A1 | 9/2010 | Goetz | |
| 2010/0232613 A1 | 9/2010 | Krause et al. | |
| 2010/0254540 A1 | 10/2010 | Bang | |
| 2010/0284556 A1 | 11/2010 | Young | |
| 2011/0176686 A1* | 7/2011 | Zaccaria | H04R 25/70 381/314 |
| 2012/0095528 A1 | 4/2012 | Miller et al. | |
| 2012/0183165 A1 | 7/2012 | Foo et al. | |
| 2013/0110195 A1 | 5/2013 | Fletcher et al. | |
| 2013/0177188 A1 | 7/2013 | Apfel et al. | |
| 2013/0274628 A1 | 10/2013 | Fausti et al. | |
| 2013/0308802 A1 | 11/2013 | Eaton et al. | |
| 2014/0146974 A1 | 5/2014 | Krueger et al. | |
| 2014/0193008 A1 | 7/2014 | Zukic | |
| 2014/0211972 A1* | 7/2014 | Kim | H04R 25/70 381/314 |
| 2014/0270211 A1 | 9/2014 | Solum et al. | |
| 2014/0334629 A1 | 11/2014 | Andersen et al. | |
| 2014/0355798 A1 | 12/2014 | Sabin | |
| 2015/0003652 A1 | 1/2015 | Bisgaard et al. | |
| 2015/0023512 A1 | 1/2015 | Shennib | |
| 2015/0023535 A1 | 1/2015 | Shennib | |
| 2015/0036851 A1* | 2/2015 | Howes | H04R 25/554 381/314 |
| 2015/0125014 A1* | 5/2015 | Howes | H04R 25/70 381/315 |
| 2015/0161344 A1 | 6/2015 | Chung et al. | |
| 2015/0172837 A1 | 6/2015 | Martinez Azkorra | |
| 2015/0181356 A1 | 6/2015 | Krystek et al. | |
| 2015/0281853 A1 | 10/2015 | Eisner et al. | |
| 2015/0289062 A1 | 10/2015 | Ungstrup et al. | |
| 2015/0351142 A1 | 12/2015 | Seymour et al. | |
| 2016/0212552 A1* | 7/2016 | Schneider | H04R 25/558 |
| 2016/0302666 A1 | 10/2016 | Shaya | |
| 2017/0142530 A1 | 5/2017 | Neumeyer | |
| 2017/0318457 A1 | 11/2017 | Westermann et al. | |
| 2018/0000651 A1 | 1/2018 | Pan | |
| 2018/0115841 A1 | 4/2018 | Apfel et al. | |
| 2018/0132046 A1 | 5/2018 | Westermann et al. | |
| 2018/0146310 A1* | 5/2018 | Bazzoni | G16H 40/67 |
| 2019/0090073 A1 | 3/2019 | Wendt et al. | |

FOREIGN PATENT DOCUMENTS

| | | | |
|---|---|---|---|
| DE | 19815373 A1 * | 10/1999 | H04R 25/70 |
| DE | 102006035011 B4 | 11/2010 | |
| DE | 102014112098 B4 | 2/2016 | |
| EP | 1701585 A2 | 9/2006 | |
| EP | 2280562 A2 | 2/2011 | |
| EP | 1596633 B1 | 7/2012 | |
| EP | 2549397 A1 | 1/2013 | |
| EP | 2876902 A1 | 5/2015 | |
| EP | 2813092 B1 | 5/2016 | |
| EP | 3064135 A1 | 9/2016 | |
| EP | 2997740 B1 | 10/2019 | |
| EP | 3221808 B1 | 7/2020 | |
| JP | 60216695 A | 10/1985 | |
| TW | 1549091 B | 9/2016 | |
| WO | 2005125280 | 12/2005 | |
| WO | 2007098605 A1 | 9/2007 | |
| WO | 2011051507 A1 | 5/2011 | |
| WO | 2011128462 A2 | 10/2011 | |
| WO | 2011147998 A2 | 12/2011 | |
| WO | 2013033872 A1 | 3/2013 | |
| WO | 2015028050 A1 | 3/2015 | |
| WO | 2015061925 A1 | 5/2015 | |
| WO | 2016174603 A1 | 11/2016 | |

OTHER PUBLICATIONS

"[Redacted Version of Document Proposed to be Filed Under Seal] Declaration of Dr. Les Atlas in Support of Defendant Sivantos GMBH's and Sivantos, Inc.'s Oppostion to Plaintiffs Motion for Preliminary Injunction," Jul. 30, 2018, 19 pages, Case No. 2:17-cv-05309-ODW (JEMx), US Dist. Ct. Central District of California.
"Declaration of Frank Beck in Support of Defendants Sivantos GMBH's and Sivantos, Inc.'s Oppostion to Plaintiff's Motion for Preliminary Injunction," Jul. 27, 2018, 8 pages, Case No. 2:17-cv-05309-ODW (JEMx), US Dist. Ct. Central District ofCalifornia.
"Expert Declaration of Dr. Gina P. Angley," May 25, 2018, 15 pages, Case No. 2:17-cv-05309-ODW (JEMx), US Dist. Ct. Central District of California.
"Reply Declaration of Dr. Caslav V. Pavlovic [Redacted Version of Document Proposed to be Filed Under Seal], " Aug. 3, 2018, 6 pages, Case No. 2:17-cv-05309-ODW (JEMx), US Dist. Ct. Central District of California.
David Fabry, Ph.D. ed. Applications of Telehealth for hearing Care, Audiology Today, Sep./Oct. 2010, 7 pages.
De Wet Swanepoel, Tele-audiology: Providing Remote Hearing Health Care, Audiology Today, Mar./Apr. 2010, 21 pages.
Dennis KC, Gladden CF and Noe CM. "Telepractice in the Department of Veterans Affairs Hearing Review," 2012;19(10):44-50.
EP 177998214—Extended European Search Report dated Oct. 15, 2019, 8 pages.
Expert Declaration of Dr. Caslav V. Pavlovic [Redacted] May 10, 2018, 28 pages, Case No. 2:17-cv-05309-ODW (JEMx), US Dist. Ct. Central District of California.
Expert Report and Disclosure of Dr. Gina P. Angley, Dec. 24, 2018, 17 pages, Case No. 2:17-cv-05309-ODW (JEMx), US Dist. Ct. Central District of California.
Letter from Erika N.D. Stanat, Harter Secrest & Emery LLP, to Carole E. Handler, Esq. at Eisner Jaffe, Dec. 1, 2016, 10 pages.
Oberon microsystems, "Hearing Aid Configuration over the Internet," paper, available from http://oberon.ch/pdf/Reference_Phonak_Teleaudiology.pdf, 2 pages.
PCT IPRP and Written Opinion in PCT/US2017/026831, dated Jun. 22, 2017, 5 pages.
Wesendahl, Theo, Hearing Aid Fitting: Application of Telemedicine in Audiology, Int'l Tinnitus Journal, vol. 9, No. 1, 56-58, Jun. 2003, 4 pages.
EP 17799823.4—Extended European Search Report dated Oct. 15, 2019, 8 pages.
EP 17799823.4—Response to Extended European Search Report dated Oct. 15, 2019, as filed on Apr. 23, 2020, 21 pages.
EP 17799823.4—Office Action dated Nov. 4, 2021, 11 pages.
U.S. Appl. No. 15/158,667—Non-Final Office Action dated Jul. 3, 2017, 19 pages.
U.S. Appl. No. 15/158,667—Final Office Action dated Jan. 10, 2018, 19 pages.
U.S. Appl. No. 15/158,667—Non-Final Office Action dated Nov. 1, 2018, 19 pages.
U.S. Appl. No. 16/428,337—Non-Final Office Action dated Jul. 3, 2019, 19 pages.
U.S. Appl. No. 16/846,184—Office Action dated Jun. 22, 2021, 11 pages.
EP 17799823.4—Response to Office Action dated Nov. 4, 2021 filed Mar. 11, 2022, 18 pages.
Wikipedia, "Wireless Power", http://en.wikipedia.org/wiki/Wireless_power, retrieved Feb. 8, 2015.
Mark Krumm, "Audiology telemedicine," Journal of Telemedicine and Telecare, Feb. 2007, pp. 224-229, vol. 13.

* cited by examiner

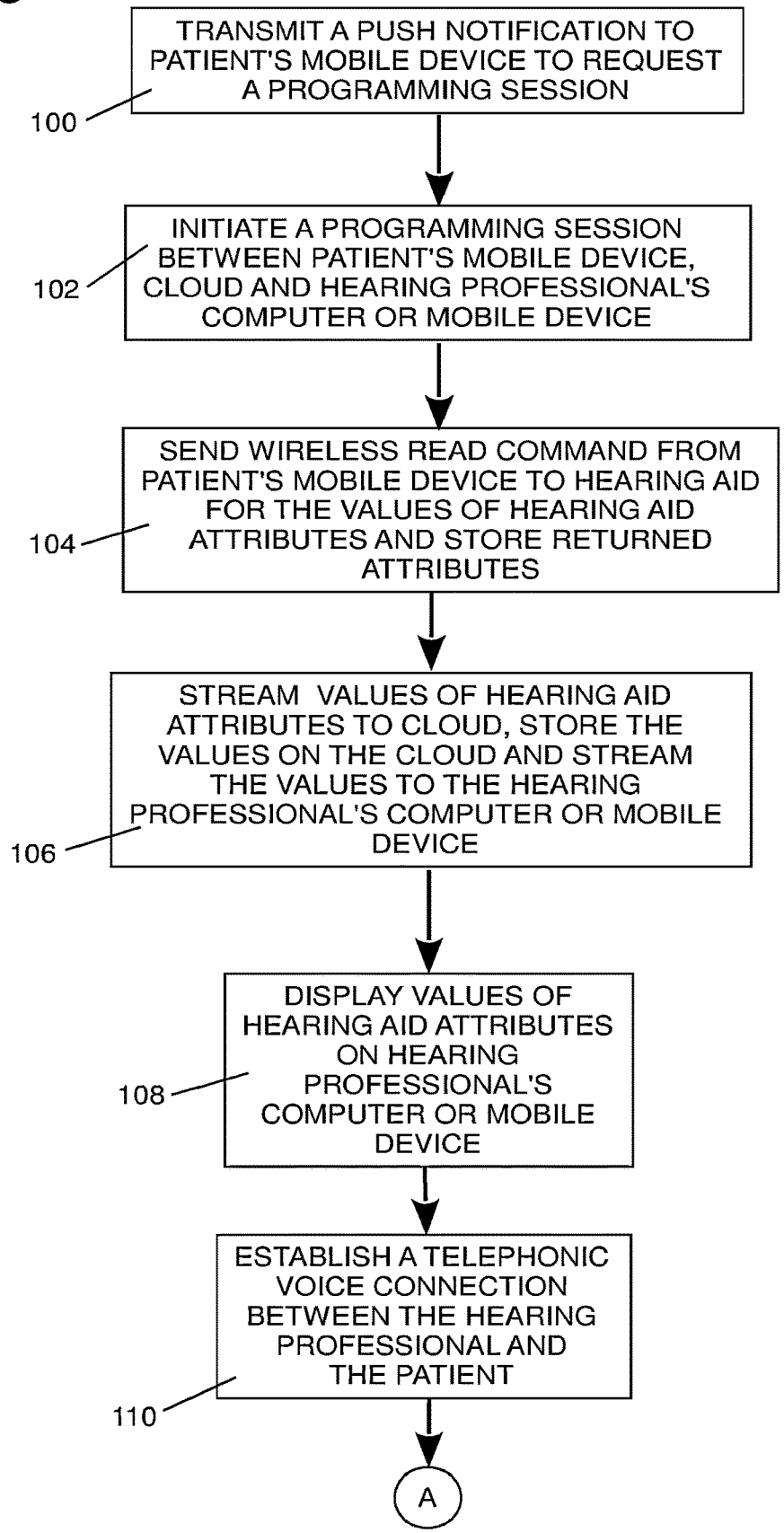

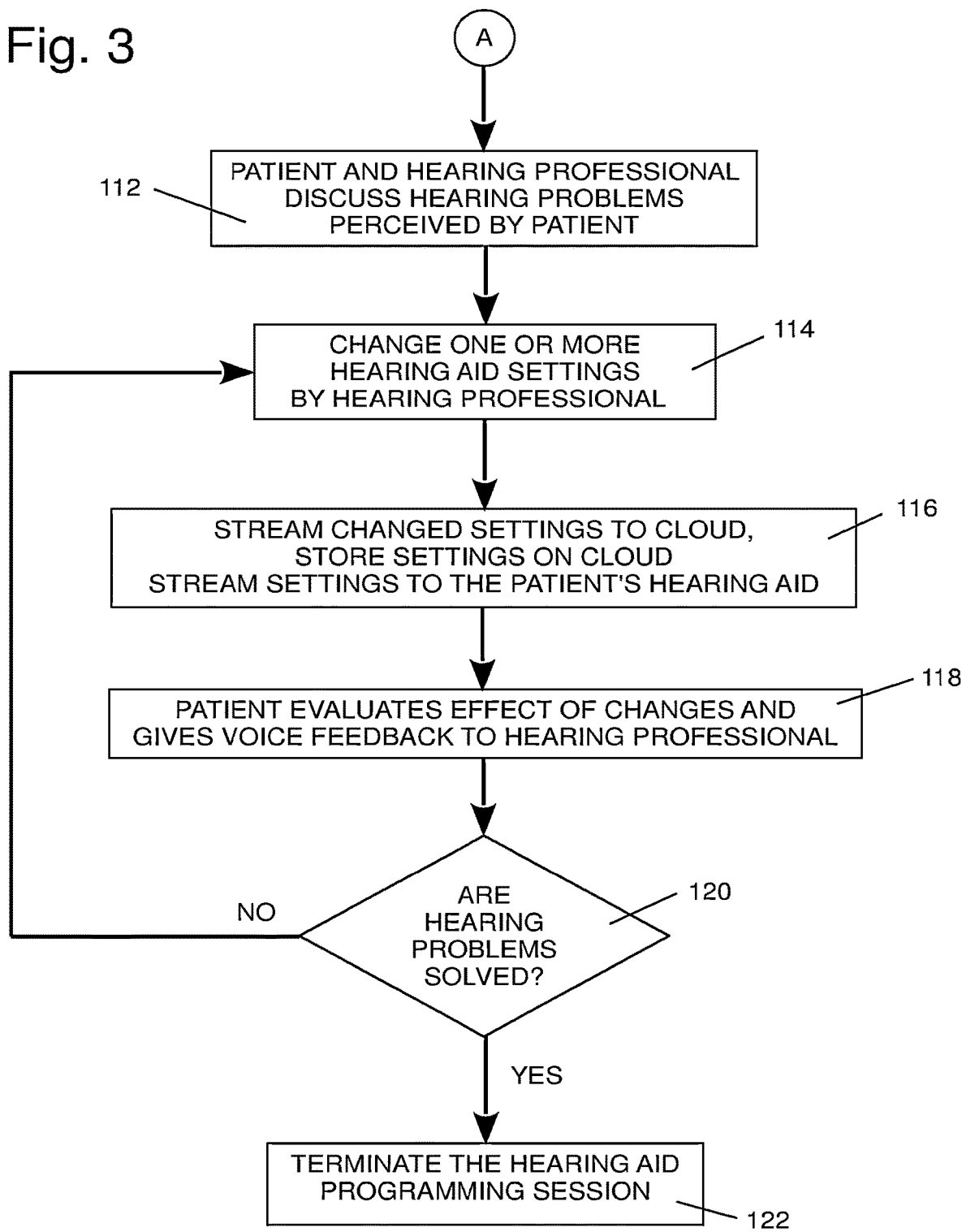

SYSTEM FOR REAL TIME, REMOTE ACCESS TO AND ADJUSTMENT OF PATIENT HEARING AID WITH PATIENT IN NORMAL LIFE ENVIRONMENT

PRIORITY

This application is a continuation of U.S. patent application Ser. No. 16/846,184 filed on 10 Apr. 2020; which application is a continuation of U.S. patent application Ser. No. 16/428,337 filed on 31 May 2019 (now U.S. Pat. No. 10,623,564); which application is a continuation of U.S. patent application Ser. No. 15/158,667 filed on 19 May 2016 (now U.S. Pat. No. 10,348,891); which application claims the benefit of U.S. Provisional Patent Application No. 62/215,032 filed 6 Sep. 2015; which applications are incorporated herein by reference.

BACKGROUND OF THE INVENTION

This invention relates generally to accessing a hearing aid remotely without the use of any hearing aid manufacturer's software or hardware. Remote access allows for direct and third party marketing to individuals wearing hearing aids and provides a practical system and method that enables a hearing professional to access and adjust a patient's hearing aid attributes not only from a location that is geographically remote from the patient but also while the patient is located in a normal, real life environment that includes background noises or other factors which make hearing more difficult for a hearing impaired patient.

Modern hearing aids are available in which the audio amplifier circuits of the hearing aid are controlled by digital data processors and signal processors which are also capable of establishing two-way data communication connections with Bluetooth-enabled computing devices such as smartphones, other mobile devices and laptop computers although only some have this ability. Such hearing aids are essentially special purpose computers that store and run programs for wireless communication according to the Bluetooth protocols and also run programs for processing the audio input signals from the hearing aid's microphone before outputting the processed audio signal to the hearing aid's output speaker. These hearing aids also store hearing aid settings which are adjustable attributes for processing the audio signal according to the algorithms used by the programs and additionally store data collected by the hearing aid programs showing characteristics of the history of the use of the hearing aid by the patient. The particular data that is stored varies substantially among the hearing aids of different manufacturers. Nonetheless, as the number and types of hearing aid attributes and collected use history data have increased, hearing professionals are able to more precisely tailor a hearing aid's characteristics to the particular hearing needs of individual patients.

A hearing professional is able to select the hearing aid attributes for each particular hearing aid and store them in the hearing aid by "programming" or "adjusting" the hearing aid. It is common in the hearing aid technological field to use the words "programming" and "adjusting" interchangeably to refer to the professional function of selecting the appropriate attributes and causing them to be stored in the hearing aid. However, some in the technological field use the word "programming" to refer to the initial selection and storing of the attributes and use the word "adjusting" to refer to subsequent selection and storing that is performed after the initial "programming". These two words are used interchangeably in this description.

Unfortunately, the current state of this technology requires a patient to make an appointment with a hearing professional and come into an office that has the necessary equipment, hardware and software for digitally or manually accessing the hearing aid data and adjusting one or more of the hearing aid settings. This personal appearance requirement imposes on the patient the inconvenience, expense and time consumption that are usually associated with travel to a remote location. This requirement is particularly problematic for patients that are not ambulatory, live in remote areas where hearing professionals are located at great distances to the patient, or live in developing countries where a hearing professional may not be available.

Additionally, the need to access and adjust the hearing aid settings while the patient is located at a professional office also limits the effectiveness of any adjustments. That limitation exists because an office is a relatively quiet and acoustically protected environment with no normal sounds, such as any of the diverse background noises from crowds, machines and other audio sources that exist as part of a patient's real life experiences. Instead, a hearing professional programs the patient's hearing aid in a quiet office environment using the specialized equipment provided by the manufacturer of the patient's hearing aid. Although the hearing aid professional exercises the best professional judgment that is possible in this protected environment, the actual effectiveness of the initial settings stored in the hearing aid by the hearing professional can only be experienced and evaluated by the patient after leaving the office and resuming the patient's normal life. The patient then must return over several weeks and sometimes months for follow-up appointments, which again requires travel to the office with a resulting repetition of the same inconvenience, expense and time consumption associated with office visits. During this return visit, the patient reports on the function of the hearing aid and the patient's experiences with it, and the hearing professional readjusts the hearing aid settings. Often, older patients have memory issues that prevent them from being able to accurately describe any issues they are having with their hearing aids.

Sometimes a patient has an initial bad experience with the hearing aid and the patient stops wearing it shortly after the first office visit. Sometimes the patient reports problems such as hearing dishes in a kitchen in an adjacent room better than the patient can hear a friend with whom the patient was having a conversation while sitting at the same table. The hearing professional then again uses professional judgement to estimate the appropriate settings changes that should be made to compensate for any problems described by the patient. This sequence of office visits for adjustment followed by a return to normal life and evaluation of the effectiveness of the adjustments is often repeated multiple times over a period of several weeks or in some cases several months until the patient is finally satisfied with the hearing aid or in some cases gives up and rejects the hearing aid. As a result, progress toward optimizing the settings for the hearing condition of the particular patient occurs in small increments and can be spread over an extensive time period.

Additionally, if a patient rejects the hearing aid, the patient is at risk for earlier and more severe cognitive issues. Research from leading institutions, such as Johns Hopkins, shows that patients, who have even a mild hearing loss and do not wear hearing aids, are at significantly increased risk for decreased cognitive abilities including earlier and more severe, short term memory loss, dementia, Alzheimer's, balance problems, and a decrease in the ability to understand speech. So when patients reject their hearing aids or are not properly fitted for whatever reasons, they are at risk for the cognitive issues stated above. Remote access provides more convenient fitting and programming which affords more opportunity for patients to be satisfied with their hearing aids and wear them, thus minimizing the potential increase in adverse cognitive effects.

There have been proposals in the prior art for adjusting some hearing aid settings by connecting a patient's hearing aid to a hearing professional over the internet. However, these proposals have been impractical and have not been widely adopted because they require that expensive specialized equipment be sent to and returned from each patient, they require that the patient have a computer, they require the patient to install specialized software, they require the patient to connect equipment, the settings that can be accessed and adjusted are limited and they lack sufficient convenience to be of practical use to a hearing aid patient. Most importantly, each manufacturer has its own hearing aid accessing hardware and software so the hearing aid patient is required to use the existing proprietary hearing aid hardware and software of their hearing aid's manufacturer's and that requires that the special hardware be shipped to the patient in order to access the hearing aid.

The present invention allows for remote access to a patient's hearing aids. The remote access of the invention: (1) does not require or use any existing manufacturers software, proprietary or non-proprietary, in order to access the hearing aid, provide marketing to the hearing aid, program the hearing aid, update the firmware of the hearing aid, or connect to third party partners and their offerings to patients; (2) makes it unnecessary to provide the patient with any special or custom hardware device for communicating with a Bluetooth-enabled hearing aid; (3) eliminates the need for office visits along with the inconvenience, expense and time consumption associated with travelling to the office of the hearing professional; (4) enables the hearing professional to hear a patient's initial complaint, adjust the adjustable hearing aid attributes or settings while the patient is located in a sound environment where the patient is currently experiencing a commonly encountered hearing problem, receive the patient's description of the effectiveness of the adjustment and make further adjustments and therefore more accurately compensate for the hearing problem in a real-life, real-time, single session with the patient; and (5) substantially shortens the lapse of time from initial physical fitting of the hearing aid to the patient until the hearing aid is satisfactorily adjusted to meet the patient's needs because more problem specific and environment specific adjustments can be accomplished in real time during each adjustment session with the hearing professional. The patient gets better results faster and therefore is more likely to acquire a more favorable perception of the hearing aid and its usefulness. That further results in greater use of and improved comfort with the hearing aid and therefore improves the patient's ability to maintain better cognitive functioning per the research.

Through the invention, hearing aid access and programming can be achieved remotely, and as such this invention eliminates the biggest barrier to online sales, which until this invention, was the lack of the ability to program the hearing aid by a hearing professional without having to go to the hearing professional's office.

This invention also affords the opportunity to provide hearing aids to patients in markets in developing countries and remote markets in any country that does not have hearing professionals that can program them on-site or without traveling great distances. With this invention, hearing aids can be sold through retailers and the programming can be performed by hearing professionals anywhere in the world.

There are additional problems solved by the invention. Sometimes a patient may wish to obtain the services of a different hearing professional for reasons such as the patient has moved, the preferred hearing professional is temporarily unavailable or dissatisfaction with the patient's current hearing professional. Currently such a change in the treating hearing professional requires a transfer of records from the office of the first hearing professional to the office of another. That process ordinarily takes several days and often requires substantial effort by the patient. The invention permits any hearing professional, including a newly employed hearing professional, to immediately access the most recent hearing aid settings of the patient and the patient's settings history and to do so with only the permission of the patient but without the necessity of participation by the patient in the transfer of the recent hearing aid settings and the settings history. The invention allows any hearing professional located anywhere in the world to quickly become familiar with the patient's needs so that the hearing professional can make advanced preparation for an adjustment session with the patient or even review the current and historical patient settings at the beginning of an adjustment session.

Furthermore, as stated above, a problem with adjusting the settings of a hearing aid while the patient is in the office of a hearing professional is that, in the office environment, there is none of the real-life background sounds encountered in normal life environments. But if a hearing aid were adjusted while the patient is in a normal life environment and the hearing professional is not in the same location, the hearing professional cannot experience and evaluate the background sounds. However, with the invention the hearing professional is able to hear the same background sounds that the patient is currently hearing in real time during an adjustment session with the patient even though the hearing professional is at a remote location. This allows the hearing professional to make a professional evaluation of those background sounds and aids in forming a judgment of the appropriate adjustments that should be made to the hearing aid settings. The patient can then describe to the hearing professional the result of the adjustment immediately after the adjustment is made so that further adjustments can be made immediately in response to the patient's description.

BRIEF SUMMARY OF THE INVENTION

The invention is a method for real time, remote access to and adjustment of the hearing aid of a patient while the patient is located in any real-life environment that is remote from a hearing professional. The access to and adjustment of the hearing aid is made from a hearing professional's computer or mobile device to a patient's mobile device or portable computer. After transmitting a session request and initiating a session, the settings from the patient's hearing aid are wirelessly streamed from the hearing aid to the patient's mobile device and from the patient's mobile device to a cloud's streaming server connected on the internet. The settings are stored on the cloud in association with an attribute designating the stored settings as the current settings. The hearing aid settings are also immediately streamed over the internet from the cloud to a hearing professional's mobile device or computer and displayed on the hearing professional's mobile device or computer. The hearing professional then changes at least one of the adjustable hearing aid settings on the hearing professional's computer. These changed settings are streamed to the cloud, stored on the cloud and streamed from the cloud to the patient's mobile device. The changed settings are then wirelessly transmitted from the patient's mobile device to the hearing aid and stored in the patient's hearing aid. A telephonic voice connection is established between the hearing professional and the mobile device which the patient can use to describe the patient's evaluation of the effect of the changed setting or settings to the hearing professional. The patient and the hearing professional can engage in repeated modifications of the hearing aid settings followed by patient evaluations of the effect of the modifications.

BRIEF DESCRIPTION OF THE SEVERAL VIEWS OF THE DRAWINGS

FIGS. 2 and 3 are two parts of a flow chart illustrating the basic steps of practicing the invention.

Figure 1:
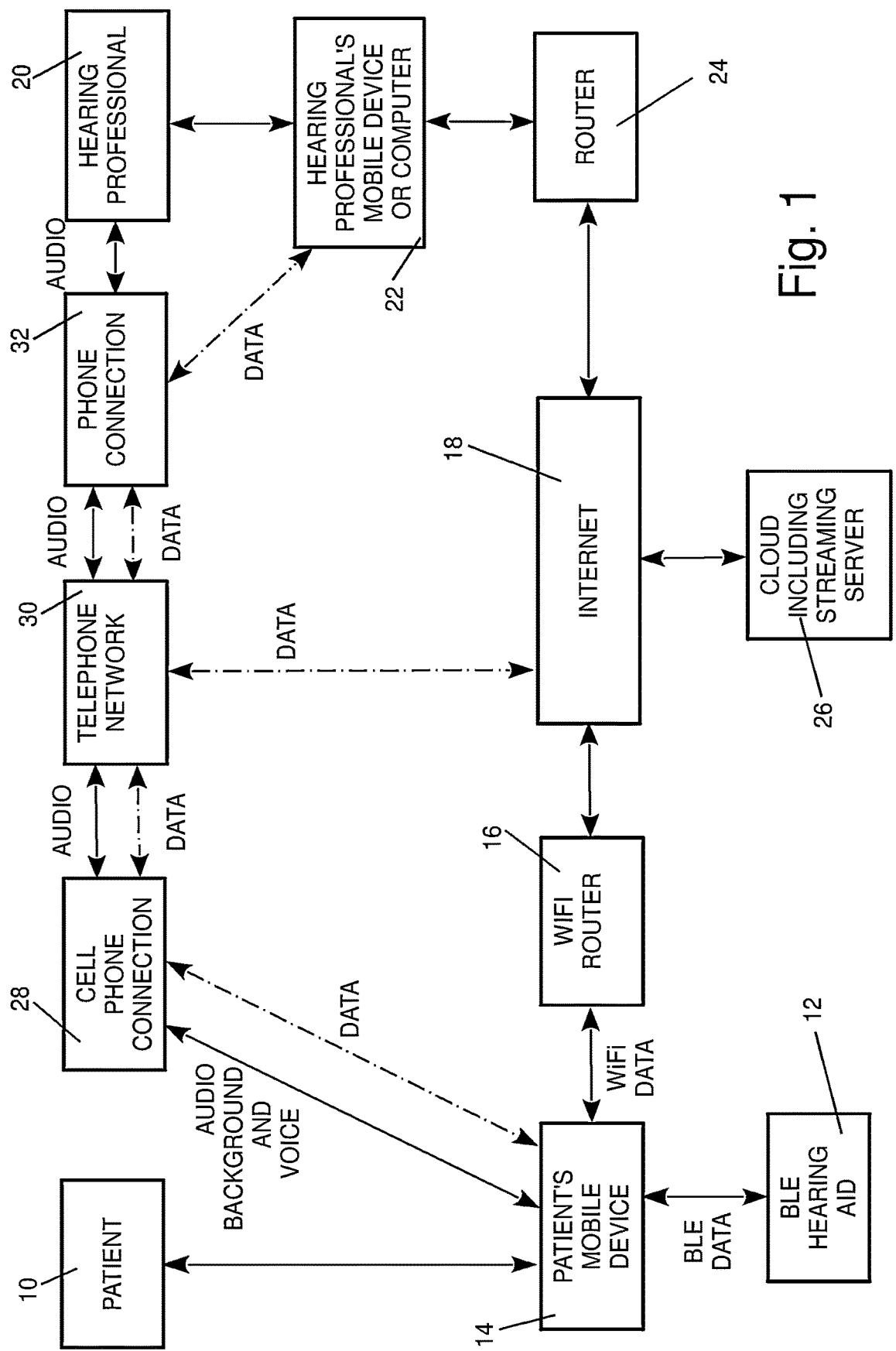
FIG. 1 is a block diagram illustrating the architecture of the components that are used in practicing the invention.

In describing the preferred embodiment of the invention which is illustrated in the drawings, specific terminology will be resorted to for the sake of clarity. However, it is not intended that the invention be limited to the specific term so selected and it is to be understood that each specific term includes all technical equivalents which operate in a similar manner to accomplish a similar purpose.

DETAILED DESCRIPTION OF THE INVENTION

Provisional patent application Ser. No. 62/215,032 filed Sep. 6, 2015 is incorporated in this application by reference.

FIG. 1 illustrates the system architecture with detail about the actors and system components used in practicing the invention. A patient 10 has a hearing aid 12 and is in possession of a mobile device 14 or computer. The term mobile device is used as a generic term referring to a smart phone, tablet or other device having the same characteristics. The mobile device 14 or computer is Bluetooth Smart (BLE) enabled for establishing wireless communication with the hearing aid 12. The mobile device 14 is WiFi enabled and may also have cellular 3G/4G service for establishing access to the internet 18. The computer can be a special purpose computer constructed for operating with the invention and having the usual computer display, digital processing and analog signal processing circuitry, and user interface with the same wireless communication capability described above, but the use of special equipment is not preferred.

In a similar manner, a hearing professional 20 is also connected to the internet most commonly through a computer 22 and router 24 which are typically used in an office. However, the hearing professional may alternatively use a mobile device for communicating with the internet.

In describing the invention the term "cloud" is used which is a relatively recent term of art. Cloud computing is a type of computing that relies on sharing computing resources rather than having local servers or personal devices to handle applications. In cloud computing different services—such as servers, storage and applications—are delivered to an organization's computers and devices through the internet. An internet-based cloud is a group of remote servers that are networked so as to allow sharing of data-processing tasks, centralized data storage, and online access to computer services or resources. It is a network of servers connected together by the internet and in some instances in part by a local area network or wide area network.

Communication over the internet between the hearing professional's mobile device 22 at one location and the patient's hearing aid 12 and mobile device 14 at a second, remote location is not a direct connection through the internet. Instead, communication in both directions between the hearing professional's mobile device 22 at one location and the patient's hearing aid 12 and mobile device 14 at a remote location is streamed from its originating source to servers on the cloud 26 on the internet and streamed from the cloud 26 to its destination. The cloud 26 comprises a streaming server and a conventional data base server. The streaming server is a data streaming cloud server, such as Firebase, which is programmed to have special qualities that allow for live data streaming and recording of two way communication between the hearing professional and the patient during an adjustment session so the server stores patient identification and patient current attribute settings data. The conventional database server is a relational database server that stores a patient's historical settings, account information and scheduling details.

Use of the cloud, including cloud storage, interposed between the patient and the hearing professional, also allows a patient to post a request for a hearing aid adjustment session. A notification of the request can be sent to the hearing professional's computer or mobile device. When the professional is available, the professional notifies the cloud which notifies the patient. When the patient is available, the hearing professional initiates an adjustment session.

In addition to the internet data connection described above, an audio connection is established between the patient 10 and the hearing professional 20 through the patient's mobile device 14, a cell tower or repeater 28, the telephone network 30 and a landline, cell tower or repeater 32 connected to the hearing professional's computer or mobile device 22 or landline phone.

In the event that a WiFi connection 16 to the internet 18 is unavailable, an alternative connection to the internet 18 can be established by a data connection through a cellular 3G/4G as illustrated by phantom lines in FIG. 1. The connection to the internet is important in order to access the cloud 26 that is interposed in the communication link between the patient and the hearing professional.

In a hearing aid adjustment or programming session, a patient's hearing aid and a hearing professional are communicating with each other in real time through the interposed cloud's streaming server while the patient is located in a normal life environment that is remote from a hearing professional. During the session, the hearing professional acquires remote access to the patient's hearing aid data and settings, and evaluates the data and settings which are displayed on the hearing professional's computer or mobile device. The hearing professional also communicates by voice with the patient, makes any appropriate changes in the hearing aid's adjustable attributes and then receives immediate feedback from the patient.

The adjustment session can be arranged by making an appointment in the conventional manner via a phone call to a professional or professional's office or by transmitting over the internet from a patient's mobile device to the cloud a request for hearing aid adjustment and an identification of the patient. If the latter method is used, the cloud transmits over the internet to the hearing professional's computer or mobile device a request for hearing aid adjustment and an identification of the patient. Use of the interposed cloud server allows the cloud server to send the session request by transmitting a push notification request to Apple's Push Notification Service or to Google's Cloud Messaging service (determined by the patient's mobile device operating system) and thereby trigger the transmission of a session request in a push notification to the hearing professional's mobile device or computer. The latter method is particularly convenient in the event that a time lapse is necessary because the hearing professional is not immediately available for an adjustment session, for example because he or she is engaged with another patient. Instead of multiple communications between the patient and the hearing professional to arrange an appointment time, a single request for a hearing aid adjustment session can be sent by the patient. Consequently, the use of the interposed cloud eliminates any requirement for simultaneous connection over the internet of the patient and the hearing professional except during a hearing aid adjustment session.

When the hearing professional is able to respond to the session request notification originating from the patient, the hearing professional can initiate a programming session. Alternatively, the hearing professional can initiate a programming session in the absence of a session request from the patient. For example, the hearing professional may believe that a sufficient period of time has elapsed since the last programming session that the patient should have a follow-up programming session or, alternatively, the patient has a previously scheduled appointment.

The basic steps in the process of the invention are summarized in FIGS. 2 and 3. To initiate a programming session, the hearing professional 20 transmits a session request over the internet from the hearing professional's mobile device or computer to the streaming cloud 26 that is accessible on the internet [step 100]. The cloud 26 is programmed so that, in response, the cloud 26 transmits a session request over the internet to the patient's mobile device 14. In the same manner as stated above, use of the interposed cloud allows the cloud server to send the session request to the patient's mobile device 14 by use of Apple's Push Notification Service or Google's Cloud Messaging service. The latter method is particularly convenient in the event that the patient is not immediately available for the programming session so that a time delay is necessary before the patient can respond to the session request. When the patient is ready to proceed after receiving the session request, the patient initiates the programming session by starting and running the application software in the patient's mobile device [step 102].

The application software sends a read command by wireless Bluetooth from the patient's mobile device to the hearing aid [step 104]. The hearing aid responds with a Bluetooth characteristic that is a data packet giving the value of the requested hearing aid attribute setting. Additional read commands are preferably sent in order to obtain all of the adjustable hearing aid attributes and the values of those settings is, at least temporarily, stored in the patient's mobile device. The values of the adjustable settings from the patient's hearing aid are then wirelessly streamed from the patient's mobile device to an internet-connected router and to the cloud 26. The adjustable settings are stored on the cloud 26 in association with an attribute designating the stored settings as the current settings and, of course, in association with an attribute that identifies the patient and preferably the patient's hearing aid. The cloud also streams those adjustable hearing aid settings over the internet to the hearing professional's computer or mobile device [step 106].

The adjustable hearing aid settings, and preferably also the non-adjustable hearing aid settings, of the patient's hearing aid are then displayed on the hearing professional's computer or mobile device so the hearing professional is able to consider and evaluate those setting and form professional opinions about their significance [step 108]. Preferably no later than this stage of the session process, a telephonic voice connection is established between the hearing professional and the patient's mobile device [step 110]. Because mobile devices include microphones and loudspeakers for respectively sensing and generating sounds, the patient and the hearing professional can engage in a discussion of hearing problems perceived by the patient [step 112].

Based upon that discussion, the hearing professional can then change at least one, and if desired, multiple adjustable hearing aid settings on the hearing professional's mobile device or computer [step 114]. The changed setting or settings are then streamed to the cloud and stored on the cloud. Additionally, the changed setting or settings are streamed from the cloud to the patient's mobile device and then wirelessly transmitted from the patient's mobile device to the hearing aid and stored in the patient's hearing aid [step 116].

Importantly, the programming session is conducted with real time streaming of the hearing aid attributes or settings data in both directions during the session between the hearing professional's computer or mobile device and hearing aid. This data is streamed between those communication endpoints. That data communication is asynchronous and the cloud is not functioning as a file server. The cloud immediately relays event changes to the destination when updates are made to the cloud's data stores.

As soon as the revised setting or settings are stored in the patient's hearing aid, the patient is immediately able to experience and evaluate the effect of the revisions on the quality of the patient's ability to hear. The patient can then describe to the hearing professional the patient's evaluation of the effect of the changed setting or settings through the telephonic voice connection [step 118].

Consequently, the invention allows the patient and the hearing professional to engage in troubleshooting by providing real-time feedback from the patient to the hearing professional while the patient is in real-life listening situations. For example in a noisy room, such as a restaurant, background noise is often proportionally greater for a hearing impaired patient than for an unimpaired person. Hearing aid adjustments are able to compensate for that problem. So, instead of making an adjustment in a quiet environment, like a hearing professional's office, the invention allows adjustment while the patient is in the problem environment so that the patient can then provide immediate voice feedback to the hearing professional about the effectiveness of the adjustment [step 120]. That allows the hearing professional to make further adjustments [step 114]. The steps of making an adjustment and receiving the patient's feedback can be repeated until the patient is satisfied or the optimum adjustments are made [steps 120 and 114]. When that happens, the programming session can be terminated [step 122]

During each programming session the attribute settings that are changed as well as other data that is stored in the hearing aid is stored on the cloud in association with a date attribute which is the date of the programming session during which the settings were changed. So a history of the changes to the hearing aid settings is available to the hearing professional for consideration during subsequent programming sessions. This same data may be temporarily stored in the mobile device and on the hearing professional's computer for use during a session. It is not necessary to store on those devices all of the settings and other data for each session although that can be done. Not only are the changed settings stored on the cloud, but preferably all the session data is stored on the cloud to give a complete history of all the hearing aid adjustments/programming. To the extent desired, sufficiently older settings data can be deleted as being obsolete because they are too old and therefore no longer relevant. Older session settings can also be recalled in cases where a patient may report to the hearing professional that the previous settings are preferred over more recent session adjustments.

An additionally desirable practice in performing the invention enables the hearing professional to hear what the patient hears in the patient's current environment. This is accomplished by transmitting through the telephonic voice connection from a microphone in the patient's mobile device environmental sounds of the patient's environment that is remote from the hearing professional. This is done in the absence of voice communication from the patient or the hearing professional to the other. This enables the hearing professional to make subjective judgments about the nature of those sounds. Additionally, conventionally used objective information, such as the sound pressure level (SPL), can also be obtained. Because the audio from the patient's environment is transmitted to the hearing professional, its audio level can be used to detect the SPL at the patient's current environment.

Some hearing aids measure and store an attribute representing the cumulative time during which the patient has turned on the hearing aid, presumably because the hearing aid was being used. From that attribute and the number of days since the last or any previous session, the proportion of the time over that time interval can be calculated and compared by the hearing professional to the typical or average daily time of hearing aid use. The hearing professional can then determine whether the patient is using the hearing aid during all, most, some or only a little each day. Additionally, if programs, for use by the patient in specific environments, such as an outdoor program or restaurant program, are programmed in the hearing aid, the hearing professional can also access information showing which programs were used and how much time the hearing aids used each of the various programs. To detect a patient's pattern of hearing aid use, the hearing aid is queried for the stored cumulative time that the hearing aid was turned on in each of the programs in the time interval between at least two dates. From the number of days between the dates the average or mean time per day that the hearing aid was in its on state is computed and then displayed for evaluation by a hearing professional.

There are numerous hearing aid attribute settings that can be modified using the present invention and they vary considerably among hearing aids from different manufacturers. In one hearing aid there are 32 different data characteristics that control everything going on in that particular hearing aid. In another more sophisticated hearing aid there are 55 data characteristics to control everything. Typical types of hearing aid attributes include frequency response, overall gain, different gains within different selected frequency ranges, volume, and attributes of filter algorithms for noise, wind, music and speech. These attributes and subdivisions or species of these attributes are used by the hearing professional to fit the hearing aid to a patient's hearing abilities, which is typically reflected in an audiogram, which is a plotting of the patients hearing according to decibel level and frequency.

The use of the cloud also allows the hearing professional to provide more conventional services to the hearing aid owner. The software applications or apps for the patient's mobile device and for the hearing professional's mobile device can be downloaded and installed and updated from the Apple Store or from Google's Play Store. The hearing professional can send automatic notifications to patients regarding battery supply status, warranty information, new product availability or an upcoming appointment. Appointments can be scheduled.

This invention also provides information to the hearing professional regarding whether or not the APP is active, working.

This invention provides information to the hearing professional regarding the working status of the hearing aid and provides trouble-shooting information and tutorials to the patient.

Firmware update notices can also be sent to patients informing them of the update availability. Integration with the hearing aid manufacturer will allow for downloading of the firmware updates through the invention. The patient will no longer have to go to a hearing professional's office to get firmware updates.

This detailed description in connection with the drawings is intended principally as a description of the presently preferred embodiments of the invention, and is not intended to represent the only form in which the present invention may be constructed or utilized. The description sets forth the designs, functions, means, and methods of implementing the invention in connection with the illustrated embodiments. It is to be understood, however, that the same or equivalent functions and features may be accomplished by different embodiments that are also intended to be encompassed within the spirit and scope of the invention and that various modifications may be adopted without departing from the invention or scope of the following claims.

What is claimed is:

1. A mobile device including an executable application supporting access to and adjustment of a patient's hearing aid, the mobile device comprising:
    a processor and memory storing a mobile application, the mobile application configured for:
        connecting to a cloud-based platform and to the patient's hearing aid;
        communicating adjustable settings for the patient's hearing aid to the cloud-based platform;
        transmitting, through a connection from a microphone cooperatively coupled with the mobile device, environmental sounds of a normal life environment;
        receiving from the cloud-based platform, a changed setting for at least one of the adjustable settings, the changed setting being stored in the cloud-based platform; and
        communicating one or more changed settings, to the patient's hearing aid for storage of the changed setting by the patient's hearing aid, thereby enabling access to and adjustment of the patient's hearing aid, wherein
    the mobile application is further configured for providing access by a hearing professional's mobile device or computer to the adjustable settings via the cloud-based platform, and
    the mobile device is configured to receive, from the cloud-based platform, a request for a session with the hearing professional, the request for the session being initiated by the hearing professional's mobile device or computer.

2. The mobile device of claim 1, wherein the mobile application is further configured for enabling communication of a patient's evaluation of the one or more changed settings from the mobile device to the cloud-based platform.

3. The mobile device of claim 2, wherein the mobile device is configured to collect user feedback.

4. The mobile device of claim 1, wherein receiving of the request for the session comprises receiving a push notification from an Apple iphone server or a Google android server that thereby triggers a transmission of a session request notification to the mobile device or a patient's computer.

5. The mobile device of claim 1, wherein the mobile device is configured to transmit to the cloud-based, platform a request for a hearing aid programming session and an identification of a patient user of the patient's hearing aid prior to initiating settings adjustment.

6. The mobile device of claim 5, wherein the request for the hearing aid programming session and the identification of the patient user of the patient's hearing aid is further transmittable from the cloud-based platform to the hearing professional's mobile device or computer.

7. The mobile device of claim 1, wherein the mobile device is configured to establish electronic voice communication between the mobile device and a hearing professional's audio link or the hearing professional's mobile device or computer.

8. The mobile device of claim 1, wherein the mobile device is configured to download the mobile application from an Apple store server or from a Google store server prior to initiating settings adjustment.

9. A mobile device including an executable application supporting access to and adjustment of a patient's hearing aid, the mobile device comprising:
a processor and memory storing a mobile application, the mobile application configured for:
connecting to a cloud-based platform and to the patient's hearing aid;
communicating adjustable settings for the patient's hearing aid to the cloud-based platform;
transmitting, through a connection from a microphone cooperatively coupled with the mobile device, environmental sounds of a normal life environment;
receiving from the cloud-based platform, a changed setting for at least one of the adjustable settings, the changed setting being stored in the cloud-based platform; and
communicating one or more changed settings, to the patient's hearing aid for storage of the changed setting by the patient's hearing aid, thereby enabling access to and adjustment of the patient's hearing aid, wherein
the adjustable settings include frequency response, overall gain, different gains within different selected frequency ranges and volumes.

10. The mobile device of claim 9, wherein the mobile device is configured so that audio is collected by a microphone in the patient's hearing aid, the mobile device, and/or a patient's computer.

11. The mobile device of claim 9, wherein the mobile device connects using wifi or a cellular connection to the cloud-based platform.

12. The mobile device of claim 9, wherein the mobile device is configured to establish wireless communication using Bluetooth with at least the patient's hearing aid.

13. A mobile device including an executable application supporting access to and adjustment of a patient's hearing aid, the mobile device comprising:
a processor and memory storing a mobile application, the mobile application configured for:
connecting to a cloud-based platform and to the patient's hearing aid;
communicating adjustable settings for the patient's hearing aid to the cloud-based platform;
transmitting, through a connection from a microphone cooperatively coupled with the mobile device, environmental sounds of a normal life environment;
receiving from the cloud-based platform, a changed setting for at least one of the adjustable settings, the changed setting being stored in the cloud-based platform; and
communicating one or more changed settings, to the patient's hearing aid for storage of the changed setting by the patient's hearing aid, thereby enabling access to and adjustment of the patient's hearing aid, wherein
the mobile device is configured so that respective changed patient's hearing aid settings are stored in association with a temporal attribute representing a current time at which a respective patient's hearing aid setting has been changed.

14. The mobile device of claim 13, wherein the adjustable settings include attributes of filter algorithms for noise, wind, music and speech.

15. The mobile device of claim 13, wherein the mobile device is configured to transmit a temporal indicator along with the temporal attribute providing a history of adjustments made to the patient's hearing aid, thereby enabling older session settings to be recalled.

16. The mobile device of claim 13, wherein the mobile device connects to the cloud-based platform through an intermediary device.

17. The mobile device of claim 13, wherein the mobile device is configured to receive audio from a patient's environment.

* * * * *